(12) United States Patent
De Baere et al.

(10) Patent No.: US 6,905,601 B2
(45) Date of Patent: Jun. 14, 2005

(54) METHOD AND DEVICE FOR ANAEROBICALLY FERMENTING ORGANIC MATERIAL

(75) Inventors: Luc Albert Omer Medard De Baere, De Pinte (BE); Piet Lodewijk Magdalena Smis, Gavere (BE)

(73) Assignee: Organic Waste Systems, Naamloze Vennootschap, Ghent (BE)

( * ) Notice: Subject to any disclaimer, the term of this patent is extended or adjusted under 35 U.S.C. 154(b) by 0 days.

(21) Appl. No.: 10/480,246
(22) PCT Filed: Jun. 19, 2002
(86) PCT No.: PCT/BE02/00101
§ 371 (c)(1),
(2), (4) Date: Dec. 15, 2003
(87) PCT Pub. No.: WO02/102966
PCT Pub. Date: Dec. 27, 2002

(65) Prior Publication Data
US 2004/0164020 A1  Aug. 26, 2004

(30) Foreign Application Priority Data
Jun. 20, 2001  (BE) .......................................... 2001/0426

(51) Int. Cl.⁷ ................................................. C02F 3/28
(52) U.S. Cl. .................... 210/603; 210/631; 210/195.3; 210/205; 210/218; 210/260
(58) Field of Search ................................ 210/603, 609, 210/631, 195.1, 195.3, 198.1, 205, 218, 252, 260

(56) References Cited

U.S. PATENT DOCUMENTS

| | | | | |
|---|---|---|---|---|
| 4,482,458 A | * | 11/1984 | Rovel et al. | 210/603 |
| 4,565,552 A | * | 1/1986 | Cotton | 48/197 A |
| 5,185,079 A | * | 2/1993 | Dague | 210/603 |
| 5,409,610 A | * | 4/1995 | Clark | 210/603 |
| 5,660,724 A | * | 8/1997 | Pollock | 210/104 |

FOREIGN PATENT DOCUMENTS

| | | | |
|---|---|---|---|
| DE | 10001107 | * | 7/2001 |
| FR | 1146820 | * | 11/1957 |
| FR | 2518116 | * | 6/1983 |
| FR | 2580294 | * | 10/1986 |
| GB | 685865 | * | 1/1953 |

* cited by examiner

Primary Examiner—Fred G. Prince
(74) Attorney, Agent, or Firm—Bacon & Thomas, PLLC

(57) ABSTRACT

Method for anaerobically fermenting biodegradable organic material, whereby this material is mixed with a quantity of already fermented material as an inoculum for the active anaerobic fermentation and this mixture is introduced at the top into a fermentation chamber (1A) in which a fermenting mass is situated, which, while being fermented, moves from an inlet (6A) situated at the top towards an outlet (8) situated at the bottom. Before the mixture is added to the fermenting mass, it is expanded beforehand until its density approximately coincides with the density of the already present fermenting mass at the beginning of this downward movement.

19 Claims, 7 Drawing Sheets

METHOD AND DEVICE FOR ANAEROBICALLY FERMENTING ORGANIC MATERIAL

BACKGROUND

1. Field

This invention relates to a method for anaerobically fermenting biologically degradable organic material, whereby this material is mixed with a quantity of already fermented material as an inoculum for the active anaerobic fermentation, and whereby this mixture is introduced at the top into a fermentation chamber in which a fermenting mass is situated, which moves from an inlet situated at the top towards an outlet situated at the bottom.

B. Related Art

By organic material, here in particular the organic fraction of domestic waste is intended, and of similar industrial waste and other organic fractions, such as, for example, slurry from water purification installations, slurry from the paper industry, or other kinds of organic slurry.

Methods for anaerobically fermenting organic waste can be divided into wet and dry manners of fermentation.

With wet fermentation methods, fresh or recycled water is added to the solid organic waste or slurry in order to form a highly liquid mash or slurry which can be pumped easily and which can easily be mixed in a fermentation tank. Such mash with 6 to 10% of dry matter, depending on the viscosity of the starting material to be treated, is pumped into a fermentation tank and is transformed into biogas, in mixed fermentation systems, in one or two phases and with mesophilic or thermophilic temperatures.

Due to the high water content of the material in the fermentation tank, the density in this tank is relatively uniform, and the produced biogas can easily escape from the mixed mash.

With a dry fermentation, on the contrary, the quantity of water which is added is limited, such that a relatively solid biologically degradable waste is pumped or pushed into a "dry" fermentation tank by means of special pumps. For organic fractions originating from domestic waste, the dry matter content of the material fed into the tank is between 15 and 45%. For more viscous materials, this may be up to 10 to 15%.

In most cases, with dry fermentation the material is pumped at the bottom into the standing tank, whereby gas is injected in order to obtain a mixing and a horizontal movement of the material. The tank may also be installed horizontally and may be provided with a mixing device which realizes the horizontal movement.

Such method of introducing the material at the bottom of a standing tank is described in WO 86/05200. Biogas is brought into the fermentation tank at different locations, through the underside, such that this underside is divided into sectors. The biogas provides for a mixing of the contents of the sectors and a movement of the fermenting mass from one sector to the other and finally towards the outlet, also situated at the bottom.

EP-A-0.476.217 describes a method, whereby a horizontal fermentation tank with therein a mixing device is used. After having been mixed with a portion of fermented material, the biodegradable material is pushed, through a feeding tube realized as a heat exchanger, into the tank and in this tank is mixed by a blender, as a result of which the fermenting mass flows horizontally through the tank, from one extremity to the other, where it is discharged at the bottom.

According to EP-A-0.205.721 and EP-A-0.577.209, the fermentation is performed in a vertical fermentation tank, without a mixing device therein. The biodegradable material is mixed with fermented material as an inoculum and is pumped into the tank at the top.

In the tank, the fermenting mass sinks, as fermenting material is discharged at the bottom. This latter is performed by means of a sliding grid moving to and fro above the flat bottom of the tank, which grid pushes this fermented material into a screw conveyor device situated therebelow. This device pushes the fermented material into another screw functioning as a lock by forming a stopper of fermented material at its conical outlet.

In the method according to EP-A-0.577.209, moreover, due to the design of the device, a fraction division into a liquid and a solid fraction is obtained, such that the content of solid matter in the fermentation tank can be maintained and that the dry matter content of the fed material, which consists of a mixture of inoculum and fresh material, is situated between 15 and 40%.

In these fermentation tanks without mixer, it is typical that the content thereof rises and expands as a result of the produced biogas. This biogas can not bubble immediately upward as in a wet tank and can not easily escape, due to the high viscosity of the material in which it is created and through which it must weave its way upward.

In practice, the material will expand as a consequence thereof, and its density will be reduced by about 10 to 40%. The average density depends on various parameters, such as the degree of biogas production, the feeding frequency, the kind of structure of the added material, and the height of the feeding tank. Depending on the feeding, the density may vary from 0.7 to 1.2 kg/l.

It was noted that this feeding matter, being a mixture of fresh biodegradable waste and fermented material or residue, has a density which mostly is higher than 1.0 kg/l, on account of the fact that the prevailing biogas during mixing of the fermented material and the fresh material can escape from the fermented material.

When this feeding matter with fresh material and inoculum, which, due to the degassification, has obtained a higher density, is brought at the top into the fermentation tank in which the material has a lower density, then, depending on the difference in density, the dimensions and the diameter of the fermentation tank and the extraction system thereof, too fast a sinking of this feeding matter through the mass in the tank can be noted, such that this feeding matter arrives faster at the bottom than the remainder of the fermenting mass and, thus, is discharged from the tank without having undergone an optimum fermentation.

BRIEF SUMMARY OF THE INVENTION

The invention aims at a method which does not have these disadvantages and whereby the mixture of fresh material and fermented material is brought at the top into a vertical fermentation chamber in which material moves downward from the top, however, whereby it is avoided that said added mixture sinks faster than the remainder of the fermenting mass.

According to the invention, the mixture, before being added to the fermenting mass and further moving downward during fermentation, is expanded beforehand until its density approximately coincides with the density of the already fermenting mass at the beginning of this downward movement.

Preferably, the mixture is beforehand expanded or reduced in density, while being moved upward.

Preferably, a mixture is made of one quantity of fresh material, together with one to ten quantities of fermented material.

Preferably, a mixture is treated, having a dry matter content of 10 to 45%.

The downward movement of the fermenting mass in the fermentation chamber can take place in a fermentation tank which is free of any mixer, whereby the mixture is supplied at the upper side of the fermentation tank, after it has been reduced in density in an expansion vessel.

The mixture can be expanded beforehand by means of a preceding biological pre-fermentation, by injecting a gas into the mixture, by beating this mixture or also by adding chemicals which lead to the release of gasses in the mixture, or by a combination of two or more of these procedures.

If the expansion or density reduction is performed by means of biological pre-fermentation, this can be performed in an expansion vessel in which the mixture remains at least 5 minutes, and preferably between 15 minutes and 3 hours.

The sojourn time in the expansion vessel also may be more than three hours, for example, 3 to 72 hours.

The invention also relates to a device which is particularly suitable for applying the method according to any of the preceding forms of embodiment.

Consequently, the invention relates to a device for anaerobically fermenting organic waste, which device comprises a fermentation tank with a fermentation chamber, an outlet for fermented material at the bottom of this tank, and a biogas outlet at the top and a feeding device comprising a mixer and which, at the top, gives out into the fermentation tank, and which is characterized in that the feeding device comprises at least an expansion vessel situated between the mixer and the fermentation tank.

The feeding device also may comprise a pump to which the mixer gives out, whereby the expansion vessel is situated between the pump and the fermentation tank.

This expansion vessel may be situated at least partially in the fermentation tank as well as at the exterior side thereof.

The expansion vessel may be reduced to a supply conduit.

DESCRIPTION OF THE DRAWINGS

The device may comprise a device for gas injection or an inlet for chemicals which lead to the release of gasses, which latter connects to the expansion vessel, the mixer or a pump connected thereto, or a beating device can be provided in the feeding device.

With the intention of better showing the characteristics of the invention, hereafter, as an example without any limitative character, several preferred forms of embodiment of a method and device for anaerobically fermenting organic material according to the invention are described, with reference to the accompanying drawings, wherein.

DETAILED DESCRIPTION OF THE PREFERRED EMBODIMENTS

Figure 1:
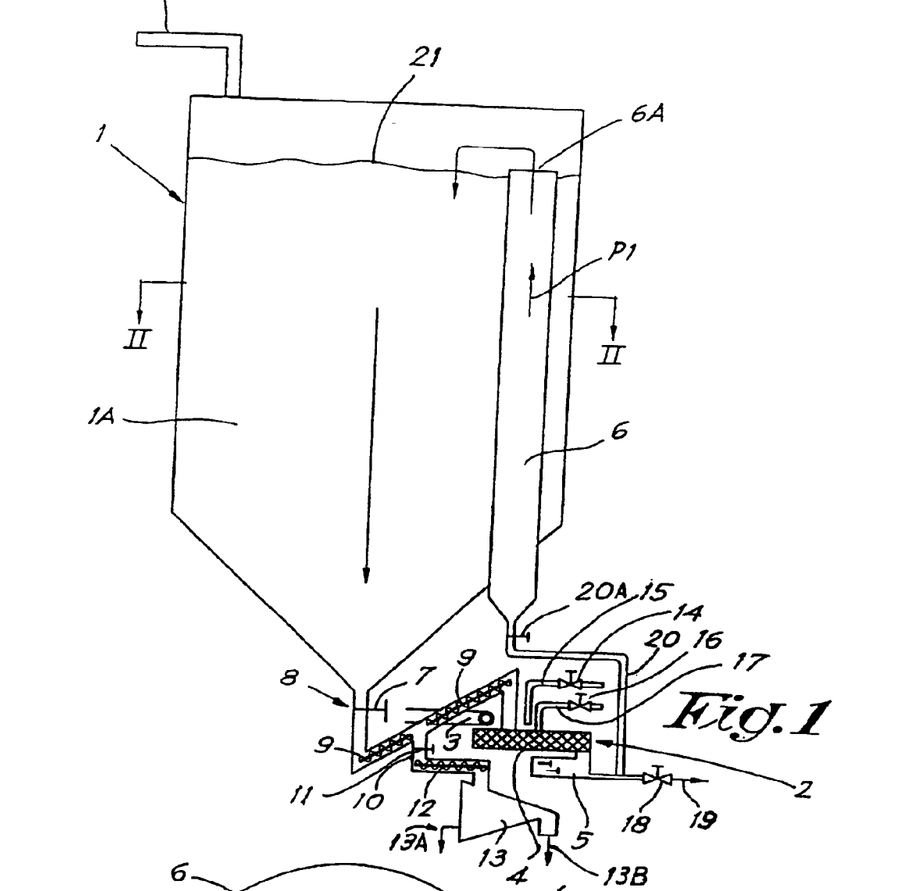
FIG. 1 schematically represents a vertical cross-section of a device for anaerobic fermentation according to the invention.
Figure 2:
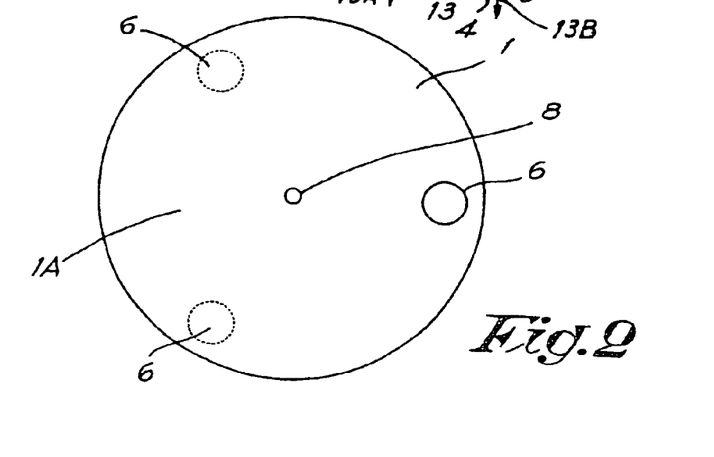
FIG. 2 represents a cross-section according to line II—II in FIG. 1.

The device for anaerobically fermenting organic material, represented in FIGS. 1 and 2, substantially consists of a closed fermentation tank 1, which comprises a fermentation chamber 1A, and a feeding device 2 comprising a transport device 3, a mixer 4, a pump 5 and an expansion vessel 6, which, at the top, gives out into the fermentation tank 1. The outlet of the expansion vessel 6 at the top forms the inlet 6A of the fermentation tank 1.

The inlet for material in the fermentation tank 1, thus, is situated at the top, and the outlet 8, which can be closed off by a valve 7, is situated below the funnel-shaped bottom of this fermentation tank 1. This fermentation tank 1 also may have a flat bottom with an outlet 8 in the bottom, possibly by means of screws of other extraction systems, or an outlet 8 at the underside of its wall.

In the outlet 8, as represented, transport screws 9 can be installed. The mixer 4 is connected to this outlet 8 and is situated below an extremity of the transport device 3, which, in the represented example, is formed by a transport conveyor. By means of this transport conveyor or another transport device, such as a screw conveyor, fresh organic material can be added to the mixer 4.

Downstream of the valve 7, a branch 10, which can be closed off by a valve 11, connects to the outlet 8, between two screws 9. In the branch 10, downstream of the valve 11, a transport screw 12 can also be arranged. The branch 10 connects to a dewatering device 13.

To the mixer 4, a water conduit 15, which can be closed off by means of a valve 14, is connected for possibly supplying water to the mixer 4, as well as a steam conduit 17, which can be closed off by a valve 16, for injecting steam in order to heat the material.

The outlet of the mixer 4 connects to the inlet of the pump 5, whereas the outlet of the pump 5, on one hand, connects to a conduit 19, which can be closed off by a valve 18, which conduit 19 serves for transporting off material, and, on the other hand, connects to the underside of the expansion vessel 6, by means of a conduit 20 which possibly can be closed off by a valve 20A.

The expansion vessel 6 penetrates into the fermentation tank 1 through the funnel-shaped bottom thereof and, with its opening, gives out into the fermentation tank 1 above the upper side of the inlet 6A, below or above the level 21 of the fermenting mass in this tank 1.

The expansion vessel 6, for example, is round, as well as the fermentation tank 1, but has a much smaller diameter.

At the top, an outlet 22 for biogas connects to the fermentation tank 1.

Fresh material to be treated is introduced into the mixer 4 by means of the transport device 3, together with a part of the fermented material which is coming through the opened valve 7 out of the fermentation tank 1 and further is transported by the screws 9 or another transport device to the mixer 4.

In the mixer 4, the fresh material and the fermented material as an inoculum are mixed in a ratio of one quantity of fresh material for one to ten quantities of fermented material.

The dry matter content of the mixture is maintained between 10 and 45% and preferably between 15 and 45% and, if necessary or desired, a quantity of water, for example, waste water, is brought into the mixer 4 through water conduit 15. This water can be supplied hot in order to bring the final mixture to a temperature of 30 to 42° C. (mesophilic) or 45 to 60° C. (thermophilic). If no water must be added, steam can be injected, by means of the steam conduit 17, into the mixer 4 in order to bring the temperature onto the desired level.

Subsequently, the mixture produced in the mixer 4 is pumped to the expansion vessel 6 through conduit 20. Valve 18 is closed and valve 20A is open. In this expansion vessel 6, the mixture moves upward, as indicated by arrow P1, whereas it undergoes a biological pre-fermentation with the production of biogas.

As a consequence thereof, the mixture will rise in the expansion vessel 6 and decrease in density. The sojourn time of the mixture in this expansion vessel 6 is at least 10 minutes and preferably is situated between 30 minutes and 3 hours.

This sojourn time is chosen such that, when, due to the pumping in of new mixture, the mixture is pushed out of the expansion vessel 6 and arrives at the top of the fermentation tank 1, its density is approximately equal to the density of the fermenting mass which already has been present at the top of this fermentation tank 1.

As a result of the formation of biogas, the density of this pre-fermented supplied mixture, due to rising, is lower than the density of the fresh supplied mixture which is pumped by the pump 5 from the mixer 4 into the expansion vessel 6.

In the fermentation tank 1, the further fermentation takes place, and the fermenting mass sinks towards the outlet 8, where it leaves the fermentation tank 1 as fermented material. The formed biogas is discharged through outlet 22.

By opening the valve 11, fermented material from outlet 8 gets into branch 10. This material is transported by the screw 12 to the dewatering device 13, where it is separated into press water 13A and a press cake 13B, which are transported off.

It is clear that the device may comprise more than one expansion vessel 6, whereby the expansion vessels 6, for example, three expansion vessels 6, are connected to the pump 5, and whereby preferably, they are equal to each other and installed in the same manner. In FIGS. 1 and 2, two additional expansion vessels 6 are represented in dashed line.

Figure 3:
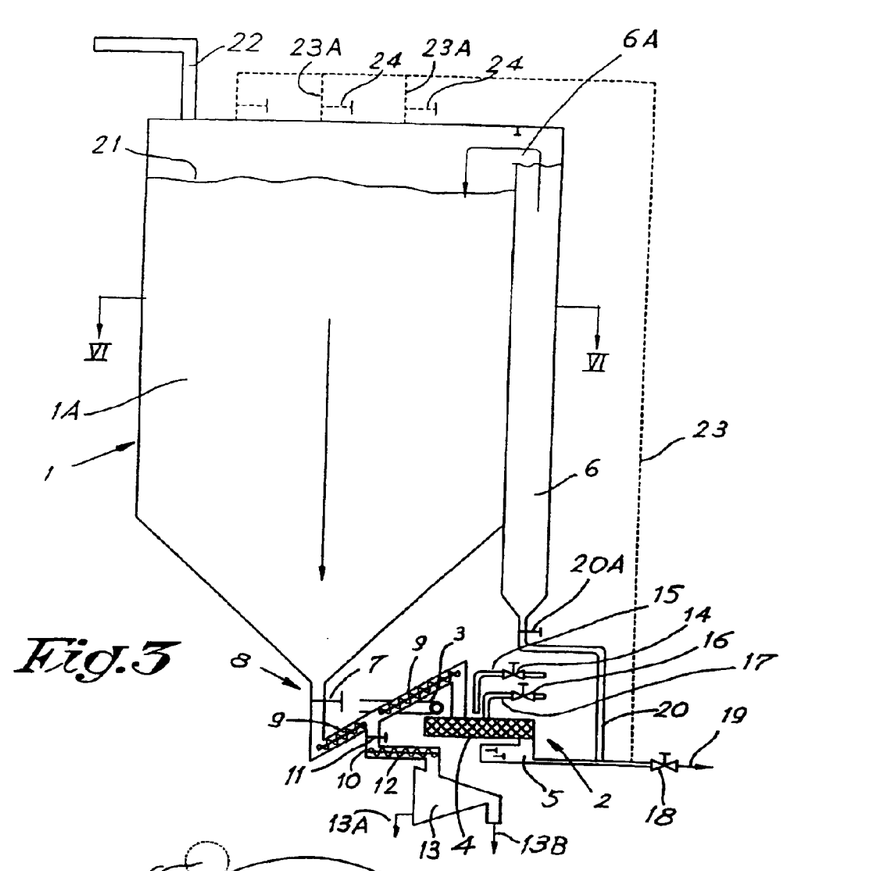
FIG. 3 schematically represents a cross-section analogous to that of FIG. 1, however, relating to another form of embodiment.
Figure 4:
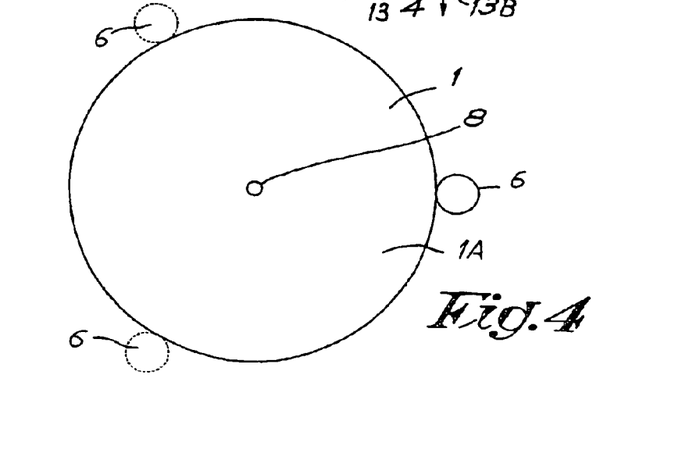
FIG. 4 represents a cross-section according to line IV—IV in FIG. 3.

The form of embodiment represented in FIGS. 3 and 4 differs from that according to FIGS. 1 and 2 in that the expansion vessel 6, expansions vessels 6, respectively, if there are several, is or are provided at the exterior side on the fermentation tank 1.

In FIG. 3, moreover in dashed line a conduit 23 is represented, which forms a bypass of the expansion vessel 6, which bypass, on one hand, connects to the conduit 19 and, on the other hand, branches off in branches 23A which give out onto the upper side of the fermentation tank 1 and can be closed off by a valve 24. The outlets of the branches in the tank 1 form the inlet 6A of this tank 1.

The functioning is as described above, however, if desired, through bypass 23, the mixture of inoculum and fresh material can be brought without expansion into the fermentation tank 1.

The expansion of the mixture of inoculum and fresh material does not necessarily have to take place by means of a pre-fermentation in an expansion vessel 6. This expansion may also be obtained by injecting gas, for example, part of the collected biogas, into the mixture, whereby, when being introduced into the fermentation chamber 1A, the mixture immediately expands, and the density thereof becomes equal to the density of the fermenting mass at the top of the fermentation chamber 1A.

This gas can be injected into the expansion vessel 6, however, this expansion vessel 6 may also be reduced to a normal conduit, for example, only the bypass 23 with the valves 24 of the form of embodiment according to FIGS. 3 and 4, whereby the gas is brought under pressure into the mixture.

Figure 5:
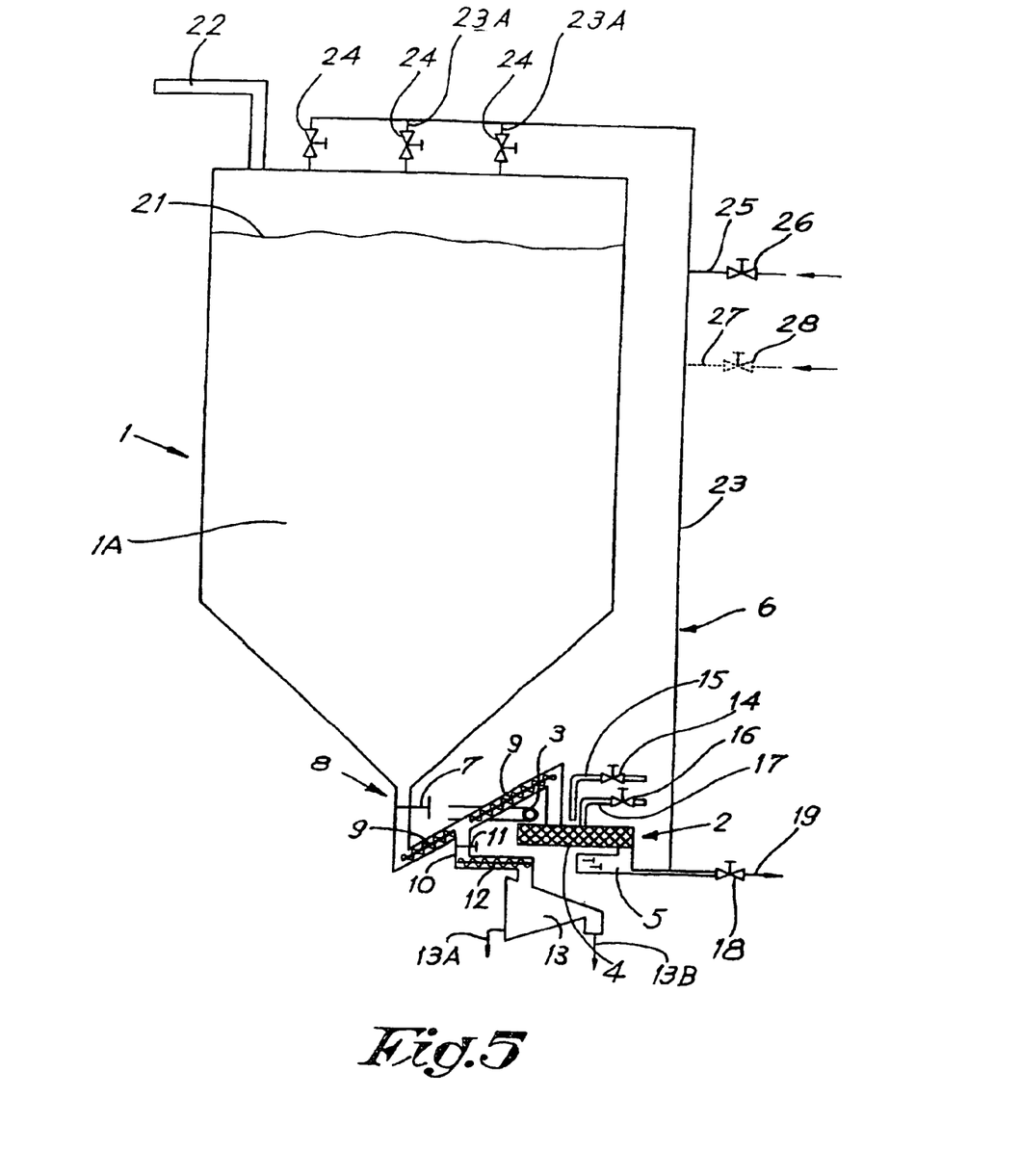
FIGS. 5 to 9 represent schematic cross-sections analogous to those of FIGS. 1 and 3, however, relating to still other forms of embodiment of the invention.

In FIG. 5, such device is represented, whereby an injection conduit 25 discharges into conduit 23, which can be closed off by a valve 26.

The same effect can be obtained by, instead of injecting gas, injecting a chemical agent which causes gas production in the mixture. In FIG. 5, in dashed line an inlet 27 of such chemical agent is represented, which connects to conduit 23 and can be closed off by a valve 28. This chemical agent which causes gas production, possibly can be added in the mixer 4 or in the pump 5.

Still another possibility for reducing the density of the mixture of fresh material and inoculum supplied to the fermentation chamber 1A and for expanding this mixture, consists in beating this mixture, for example, in the expansion vessel 6.

Figure 6:
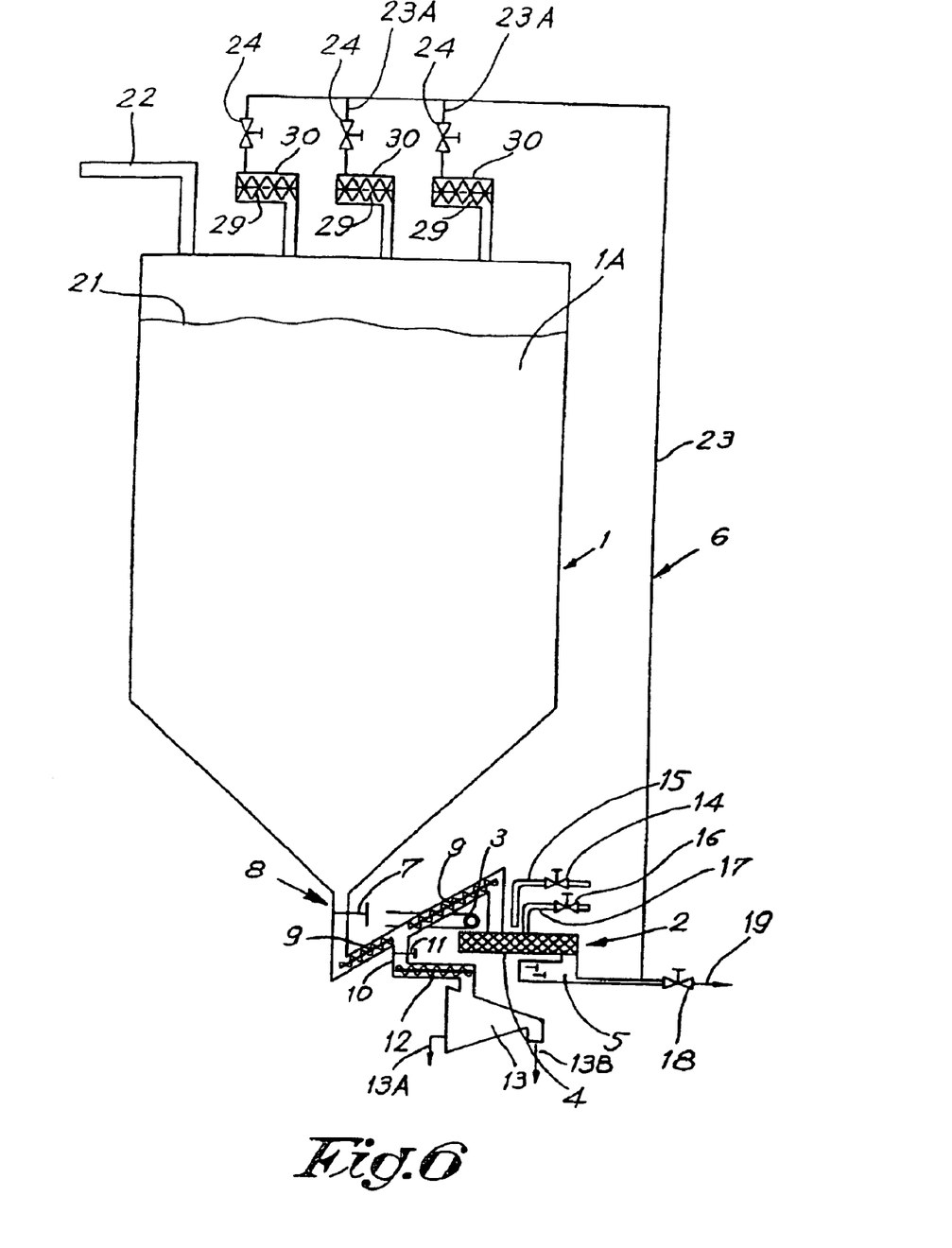

In this case, too, the expansion vessel 6 can be a reduced conduit 23, whereby the beating can take place by beating devices 29 in chambers 30 in the branches 23A of this conduit 23, as represented in FIG. 6.

The expansion vessel 6 does not necessarily have to extend over the entire height of the fermentation tank 1. It may, for example, be a vessel which connects to the fermentation tank 1 at the exterior, at half the height.

The device does not necessarily have to comprise a pump 5. Instead of a pump, it may comprise another transport mechanism, such as a screw or the like.

The expansion vessel 6 may also be formed by one or more compartments 32, defined by partitions 31, of a vertical tank 33, whereby then the space outside of the compartment 32 or the compartments 32 forms, form, respectively, the fermentation tank 1 with the fermentation chamber 1A.

It is essential that the compartment 32 or the compartments 32 discharges or discharge respectively, at the top of the fermentation chamber 1A, and allow for a certain upward flow of the mixture to be fermented.

Figure 7:
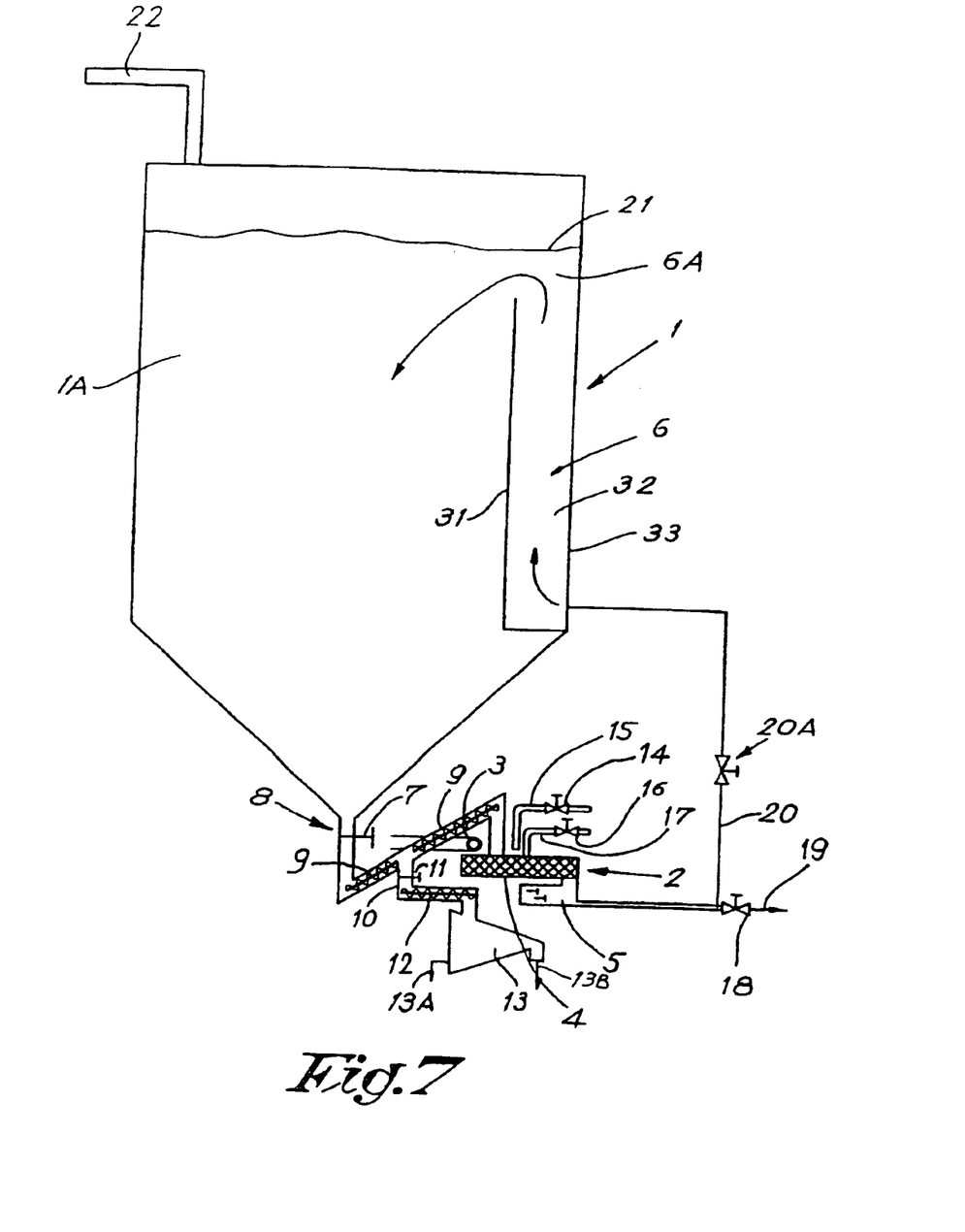

In FIG. 7, a device with such tank 33 is represented. A partition 31, situated above the conical bottom of the tank 33, together with a part of the wall of the tank 33 forms a compartment 32 which is closed at the bottom and open at the top. The mixture of fresh material and inoculum is introduced into this compartment at the bottom, where it is expanded by means of biological pre-fermentation.

Figure 8:
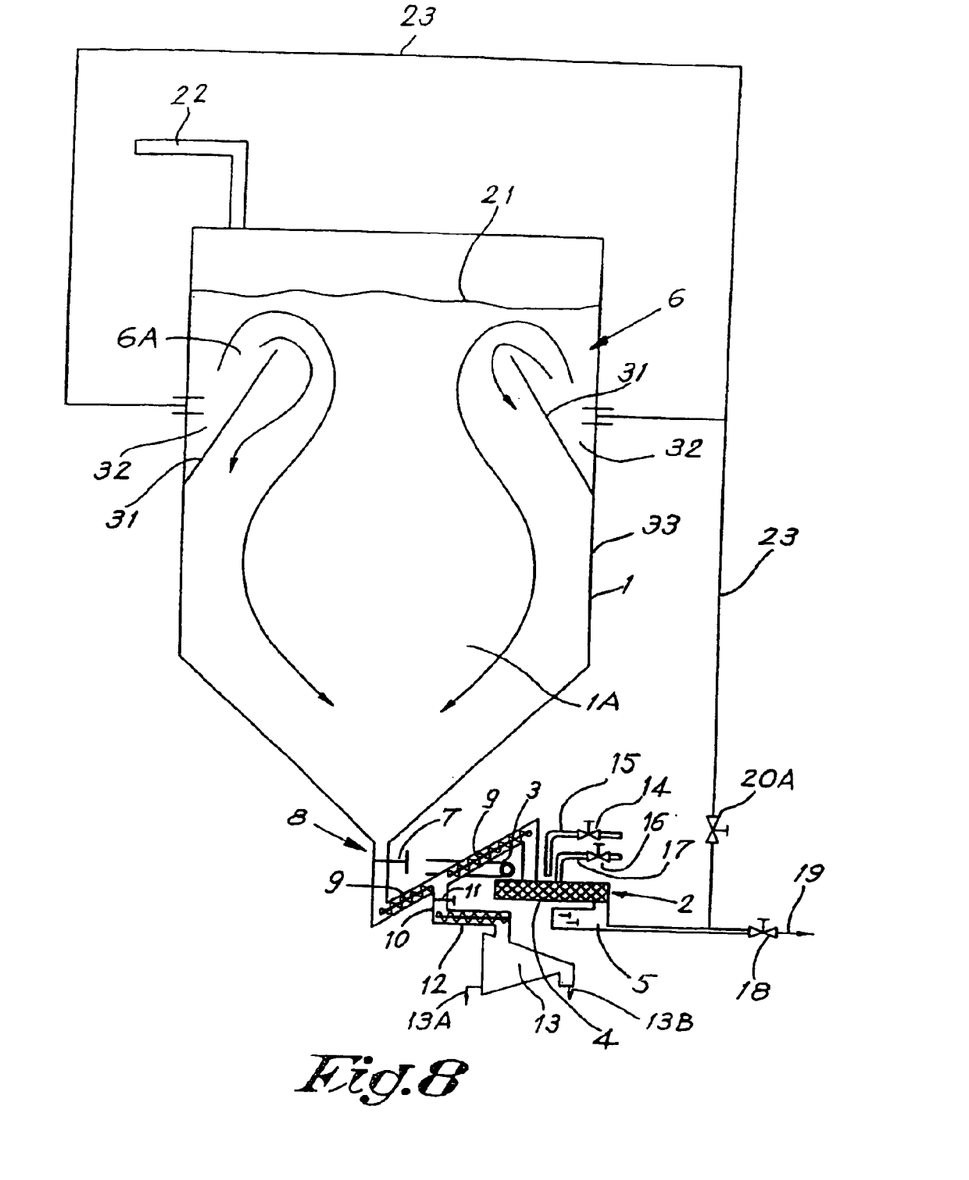

In FIG. 8, a similar device is represented, however, in this case the partition 31 is directed upwardly inclined, starting from the inside of the tank. As represented, this ring can be provided over the entire inner circumference of the tank 33, such that the compartment thus forms a circle-shaped gutter, or can be provided locally, such that several trough-shaped compartments 32 are formed at the interior side of the tank 33, which latter compartments form an expansion vessel 6.

Figure 9:
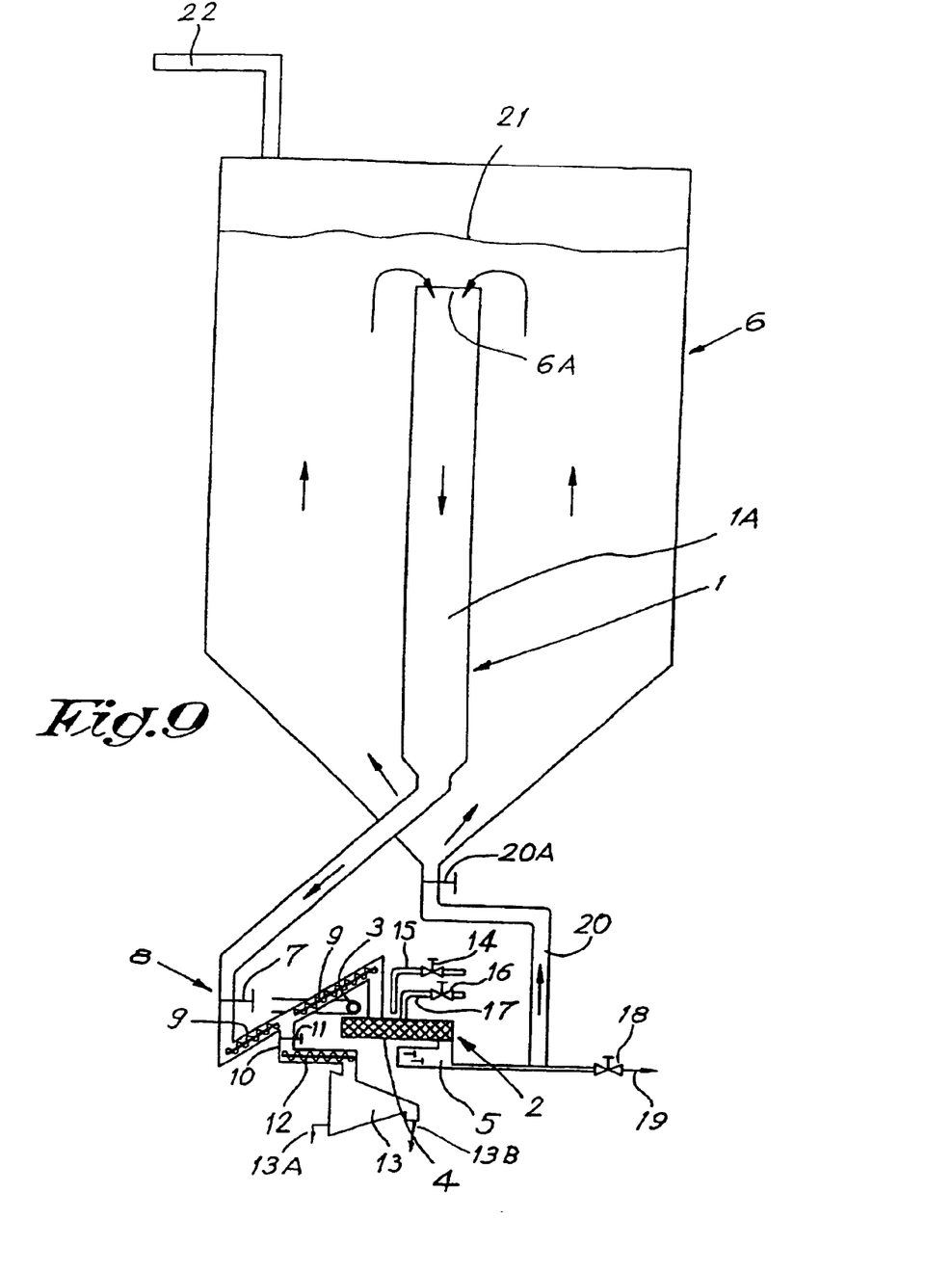

The expansion vessel 6 may not only be situated at an interior side of the fermentation tank 1, as represented in FIGS. 1 and 2, however, it may also be situated centrally, around the fermentation tank 1, as represented in FIG. 9.

This fermentation tank 1 then is formed by a tubular element which is open at the top and which protrudes with one outlet 8 through the funnel-shaped bottom of expansion vessel 6.

The invention is in no way limited to the forms of embodiment described in the aforegoing and represented in the figures; on the contrary, such method and device for anaerobically fermenting biodegradable material may be realized in different variants, without leaving the scope of the invention.

What is claimed is:

1. Method for anaerobically fermenting biodegradable organic material, wherein the organic material is mixed with a quantity of already fermented material as an inoculum for the active anaerobic fermentation to produce a mixture and the mixture is introduced at the top into a fermentation chamber in which a fermenting mass is located and which mixture, while being fermented, moves from an inlet located at a top of the chamber towards an outlet located at a bottom of the chamber, comprising the steps:
   expanding the mixture before the mixture is being added to the fermenting mass; and
   moving the expanded mixture downward during fermentation until the mixture density approximately coincides with the density of fermenting mass in the chamber at the beginning of the downward movement.

2. Method according to claim 1, wherein the mixture beforehand is expanded or is reduced in density, while being moved upward.

3. Method according to claim 1 wherein the mixture is made of one quantity of fresh material, together with one to ten quantities of fermented material.

4. Method according to claim 3, wherein the mixture comprises biologically fresh material and fermented material, and the mixture has a dry matter content of 10 to 45%.

5. Method according to claim 1, wherein the downward movement of the fermenting mass in the fermentation chamber is carried out in a fermentation tank which is free of any mixer, and the mixture is introduced at the upper side of the fermentation tank after it has been expanded in an expansion vessel.

6. Method according to claim 1, wherein the mixture is expanded by a method selected from the group consisting of: a preceding biological pre-fermentation; an injection of a gas into the mixture; a beating of the mixture; and an addition of chemicals to the mixture which causes the formation of gas in the mixture, and combinations thereof.

7. Method according to claim 6, wherein the expansion is performed by a biological pre-fermentation carried out in an expansion vessel in which the mixture remains at least 5 minutes.

8. Method according to claim 6, wherein the sojourn time of the mixture in the expansion vessel during expansion is 3 to 72 hours.

9. Device for anaerobically fermenting organic waste, comprising a vertical fermentation tank, an outlet for fermented material at a bottom of said tank, and an outlet for biogas at a top of the tank, and a supply device comprising a mixer which discharges into the fermentation tank at the top thereof, wherein the supply device comprises at least one vertical expansion vessel which is located between the mixer and the fermentation tank.

10. Device according to claim 9, wherein the supply device comprises a pump in communication with the mixer and wherein the expansion vessel is located between the pump and the fermentation tank.

11. Device according to claim 9, wherein the expansion vessel is located at least partially within the fermentation tank.

12. Device according to claim 9, wherein the expansion vessel is installed on an exterior side of the fermentation tank.

13. Device according to claim 9, wherein the expansion vessel comprises a compartment defined by at least one partition and the interior wall of a tank, and a chamber of the tank located next to the compartment forms the fermentation tank.

14. Device according to claim 9, wherein the expansion vessel completely surrounds the fermentation tank.

15. Device according to claim 9, wherein the expansion vessel comprises a conduit.

16. Device according to claim 9, including an injection device for gas, or an inlet for at least a chemical agent which causes gas production, said injection device or inlet connected to the expansion vessel, to the mixer or to a pump connected to the mixer.

17. Device according to claim 9, including a beating device in the expansion vessel.

18. Device according to claim 15, wherein the conduit includes branches, discharging onto the upper side of the fermentation tank and wherein the branches include, chambers each having a beating device therein.

19. Device according to claim 9, wherein the fermentation tank has a flat bottom.

* * * * *